United States Patent
Souris

[19]

[11] Patent Number: 6,033,216
[45] Date of Patent: Mar. 7, 2000

[54] MANDIBULAR ARCH DEVELOPER

[76] Inventor: George A. Souris, 25927 Byron Dr., North Olmsted, Ohio 44070

[21] Appl. No.: 09/246,482

[22] Filed: Feb. 9, 1999

[51] Int. Cl.⁷ ........................................................ A61C 3/00
[52] U.S. Cl. ..................................... 433/7; 433/18; 433/21
[58] Field of Search .................................... 433/7, 17, 18, 433/19, 21, 22

[56] References Cited

U.S. PATENT DOCUMENTS

| | | |
|---|---|---|
| 1,582,570 | 4/1926 | Brust ............................................ 433/7 |
| 2,141,190 | 12/1938 | Linde ........................................... 433/7 |
| 2,262,108 | 11/1941 | Linde .......................................... 433/10 |
| 2,318,001 | 5/1943 | Linde .......................................... 433/10 |
| 3,162,948 | 12/1964 | Gerber ......................................... 433/7 |
| 3,256,602 | 6/1966 | Broussard et al. ........................... 433/21 |
| 4,424,034 | 1/1984 | Dahan ......................................... 433/18 |
| 4,573,914 | 3/1986 | Nord ............................................ 433/18 |
| 4,713,000 | 12/1987 | Rosenberg .................................. 433/18 |
| 4,802,849 | 2/1989 | Collins, Jr. .................................. 433/19 |
| 5,645,422 | 7/1997 | Williams ..................................... 433/7 |
| 5,829,970 | 11/1998 | Yousefian .................................... 433/21 |

*Primary Examiner*—John J. Wilson
*Attorney, Agent, or Firm*—D. Peter Hochberg; William H. Holt

[57] ABSTRACT

A mandibular arch expander for moving the lower teeth of an individual in better alignment with the upper teeth of the individual. The expander includes a first orthodontic band and a second orthodontic band attachable to opposite molars on each side of a patient's lower mouth. A first and second attachment device is provided for bonding to at least one tooth located between the lower molar and the incisor teeth. An expansion mechanism is provided for widening the mandibular arch near the front incisor teeth. The expansion mechanism is located between the first and second attachment device. A first helical spring apparatus is located between the first attachment device and the first orthodontic band and is actuable for applying both rotational and linear forces to the first molar tooth. A second helical spring apparatus is located between the second attachment device and the second orthodontic band and is actuable for applying both rotational and linear forces to the second molar tooth.

26 Claims, 2 Drawing Sheets

MANDIBULAR ARCH DEVELOPER

BACKGROUND OF THE INVENTION

1. Field of the Invention

The present invention relates generally to orthodontic devices, and more particularly to a mandibular arch developer for moving the lower teeth of an individual in better alignment with the upper teeth.

2. Description of the Prior Art

Mandibular arch developers are used by orthodontists to move the lower teeth of an individual in better alignment with the upper teeth. This is done by lengthening and widening the jaw through application of force in specific locations on an individual's lower teeth and bone with an orthodontic appliance. The appliance can be either fixed or removable. Most of the individuals or patients using this apparatus are children, and the growth of the patient contributes to the movement of the mandibular arch. However, in some situations it is desired to move the teeth in the lower jaw of an adult. Regardless of the patient's age, these devices are used to move the lower teeth into alignment with the upper teeth and/or jaw.

In some cases, a device is necessary for expanding the position of the teeth in the lower jaw of an individual, so that the lower teeth will line up with the upper teeth prior to the placement of braces. Some of these devices may be also used to lengthen the lower jaw and allow adequate space for alignment of the lower teeth. The speed and amount of tooth movement of these devices can be effected by the growth of an individual. Other devices are adjustable by an orthodontist prior to installation in the mouth. Most of these devices require multiple mechanical parts that must be precisely machined. Many of these devices are not adjustable once they are cemented in the mouth, or may only be adjustable in a single direction. Devices that are used to both widen and lengthen the arrangement of teeth in the jaw can cause unwanted rotation of the molar teeth during the expansion process. Further, the molar teeth of some individuals are already rotated to undesired positions. None of the prior art mandibular arch developers address the problem with the unwanted rotation and/or the unwanted rotated position of the molar teeth.

It is known in the prior art to use a device known as a lip bumper. The lip bumper is used to widen and lengthen the arrangement of teeth in the jaw, but depends solely on the growth and muscle function of the patient to work. The lip bumper is placed between the lower teeth and the lower lip of a patient. As the patient grows, the jaw will move forward and force the bumper to make contact with the lip causing the arch to widen and lengthen. The lip bumper is completely dependent on the growth rate of the child and cannot be used on adults. The dependency on the growth rate of the child can cause unpredictable and inconsistent results. Further, the lip bumper has been known to occasionally cause sores in the patient's mouth resulting in pain and discomfort.

Other devices are known that are adjustable by an orthodontist and are not completely dependent on the growth rate of a patient. For example, U.S. Pat. No. 4,573,914 discloses a fixed type formative orthodontic appliance employed to increase dental arch size and overcome crowded teeth. The patent teaches both a lower and an upper appliance. The lower appliance includes an arch wire that applies force to the lower incisors by means of an arm assembly connected to oppositely disposed molar bands. A special screw assembly is located on the arm assembly adjacent each molar band. Fixedly adjoined to each of the bands is a clasp that extends along the pre-molars and applies an outward force to the teeth from the molar to the pre-molar area. The arch of the clasp is set prior to installation of the device into a patient's mouth and is not adjustable once installed. The special screw assembly attached to the arm is adjustable to vary the force on the incisors for lengthening the jaw. The device is a permanent fixture and allows access to the screw assembly, such that adjustment may be made while the appliance is in place in the patient's mouth in the lengthening direction. The screw and arm assembly is made of precisely machined parts. The device may cause the molar teeth to rotate as the device expands the mandibular arch.

U.S. Pat. No. 5,645,422 discloses a lower mandibular arch expander having a mid-arch expansion screw positioned between two forward orthodontic bands adapted to be attached to the mandibular first primary molars. A spring loaded rod and tube assembly extends between each of the front bands to a rear orthodontic band attached to the permanent first molar. The spring loaded rod and tube assembly includes a hollow tube extending from the rear orthodontic band adapted to receive a rod extending from the front orthodontic band. A coil spring is positioned around the rod and the rod is slidingly engaged in the tube. The coil springs have a preset tension that is selected by the orthodontist to affect the appropriate distal arch length development in the bicuspid area. Once this spring is set and the device installed in the mouth of the patient, the spring is no longer adjustable. The expansion screw is the only adjustment means associated with this device once the device is installed in the patient's mouth. The device will cause the rotation of the molars during mid-arch expansion. Further, the device requires two front orthodontic bands that can be seen in the patient's mouth by an observer.

The current invention eliminates the problems with the prior art by providing a mandibular arch expander that applies not only linear forces in the widening and lengthening directions, but also a rotational force about an axis of the molar tooth. The forces are applied at lower positions on the teeth than prior art devices. This application of force at a lower position eliminates tipping of the molar and provides for better centering. The device lengthens and widens the position of teeth in the lower jaw, while also rotating the molars back to their original position or to an improved position during the expansion process. The device is inexpensive and simple to make, is permanently affixed inside the patient's mouth once installed, can be used on children and adults, does not cause sores in a patient's mouth, is not noticeable by the ordinary observer while in a patient's mouth and is simple to adjust in all three directions in or out of the patient's mouth.

SUMMARY OF THE INVENTION

In accordance with a preferred embodiment of the invention, a mandibular arch expander is provided for moving the lower teeth of an individual in better alignment with their upper teeth. The expander includes a first orthodontic band and a second orthodontic band attachable to opposite molars on each side of a patient's lower jaw. A first and second attachment means is provided, each being adapted to be affixed to at least one tooth. A first spring means, located between the first attachment means and the first orthodontic band, is actuable for applying both rotational and linear forces to a first molar tooth when the first orthodontic band surrounds and is affixed to the first molar tooth. A second spring means located between the second attachment means and the second orthodontic band is actuable for applying both rotational and linear forces to a second molar tooth, located on the opposite side of the mouth from the first molar tooth, when the second orthodontic band surrounds and is affixed to the second molar tooth.

In a preferred aspect of the invention, a mandibular arch expander is provided for moving the lower teeth of an individual in better alignment with their upper teeth on only one side of the mouth. In this case the expander includes an orthodontic band adapted to fit over a lower molar. An attachment means is provided which is adapted to be affixed to at least one tooth. A spring means is located between the first attachment means and the first orthodontic band and is actuable for applying both rotational and linear forces to the molar tooth when the orthodontic band surrounds and is affixed to the molar tooth.

In another preferred aspect of the invention, a mandibular arch expander is provided for moving the lower teeth of an individual in better alignment with the upper teeth. The expander includes a first orthodontic band and a second orthodontic band, both of the bands being adapted to fit over a lower molar tooth. Further, a first and a second metal framework assembly are provided, and each of the metal framework assemblies include at least one rod member adaptable to be affixed to at least one tooth between the molar tooth and the incisor teeth. The expander includes expansion means for widening the mandibular arch at a location near the front incisor teeth of an individual. The expansion means is located between the first and second metal framework assemblies. A first spring means is disposed between the first metal framework assembly and the first orthodontic band. The first spring means includes a first vertical helix spring that is actuable for applying a force to the first molar tooth both back and away from the lower incisor teeth, a first horizontal helix spring that is actuable for applying a rotational force to the first molar tooth and a first connecting wire that is actuable for applying a force toward the cheek of an individual, when the first orthodontic band surrounds and is affixed to the first molar tooth. The first connecting wire connects the first horizontal helix spring and the first vertical helix spring. A second spring means is provided, which is disposed between the second metal framework assembly and the second orthodontic band. The second spring means includes a second vertical helix spring that is actuable for applying a force to the second molar tooth both back and away from the lower incisor teeth, a second horizontal helix spring that is actuable for applying a rotational force to the second molar tooth and a second connecting wire that is actuable for applying a force toward the cheek of an individual, when the second orthodontic band surrounds and is affixed to the second molar tooth. The second connecting wire connects the second horizontal helix spring and the second vertical helix spring.

It is an object of the present invention to provide a mandibular arch expander for expanding the mandibular arch of a child or an adult.

Another object of the present invention is to provide a mandibular arch expander that is adjustable while it is either in or out of a patient's mouth.

Another object of the present invention is to provide a mandibular arch expander that provides consistent results and is comfortable for the patient to wear.

Yet another object of the invention is to provide a mandibular arch expander that is hidden from the sight of an ordinary observer once installed in a patient's mouth.

It is another object of the present invention to provide a mandibular arch expander that can provide a rotating force on the back molars to urge the back molars to their original orientation or a preferred position in addition to a force for lengthening the arrangement of teeth in the jaw and a force for widening the arrangement of teeth in the jaw.

Another object of the present invention is to provide a mandibular arch expander that requires little or no maintenance.

It is a further object of the invention to provide an effective mandibular arch expander that is both inexpensive to make, light in weight and easy to install and remove.

These and other objects will become apparent with the following description of the preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DESCRIPTION OF THE PREFERRED EMBODIMENT

Figure 1:
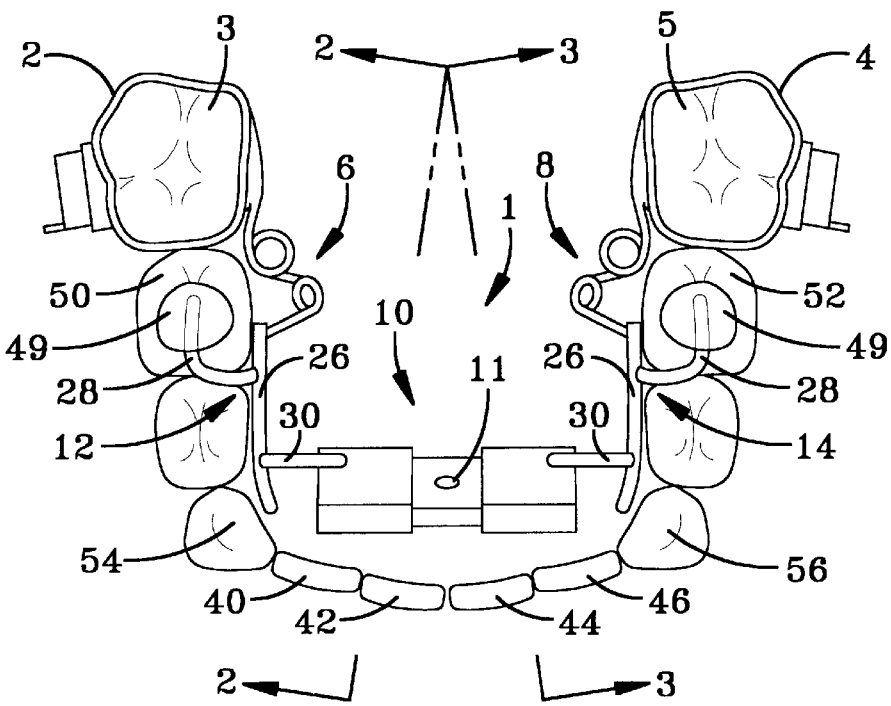
FIG. 1 is a plan view of the mandibular arch expander of the present invention attached to a mold of the mandibular arch.

Referring now to the drawings wherein the showing are for the purpose of illustrating the preferred embodiment of the invention only, and not for the purpose of limiting the same, FIG. 1 shows a mandibular arch developer 1 including a pair of orthodontic bands 2 and 4, each adapted to receive and be secured to molars 3 and 5, respectively. The bands 2 and 4 are placed partially around molars 3 and 5 and cemented by conventional means. Preferably, bands 2 and 4 are cemented to a patient's six year molars if the patient is a child. A first metal framework assembly 12 is provided, which is adapted for cementing to the teeth between molar 3 and front incisor teeth 40 and 42 with white composite cement 49. A second metal framework assembly 14 is also provided and is adapted to be cemented to the teeth between molar 5 and the incisor teeth 44 and 46. The metal framework assembly includes a central rod member 26, a first arched arm rod member 28 and a second arched arm rod member 30. An expansion screw mechanism 10 connects metal framework 12 to metal framework 14. The expansion screw mechanism 10 is disposed in a location adjacent the front incisor teeth 40, 42, 44 and 46. The expansion screw mechanism 10 is provided with a key hole 11 that allows adjustment for widening the mechanism 10, so as to provide force to the lower teeth in the widening direction. This causes the mandibular arch to expand at the front of the mouth near the canine and pre-molar areas. It should be appreciated that the expansion screw mechanism could be replaced by other expansion mechanisms, such as a spring mechanism, a piston and rod assembly, or a screw and rod mechanism.

Importantly, expander 1 includes a first spring apparatus 6 that connects metal framework assembly 12 to orthodontic band 2. A second spring apparatus 8 connects metal framework assembly 14 to orthodontic band 4. The first and second spring apparatuses 6 and 8, the first and second metal frame work assemblies 12 and 14, and the first and second orthodontic bands 2 and 4 are identical and explanation of one will provide understanding of both the assembly and operation of both.

Figure 2:
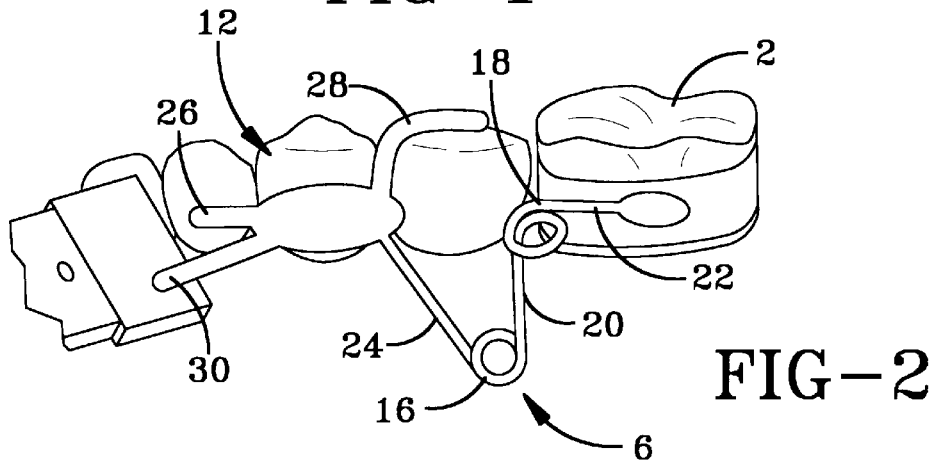
FIG. 2 is a cross-sectional view taken generally along the line 2—2 of FIG. 1.
Figure 3:
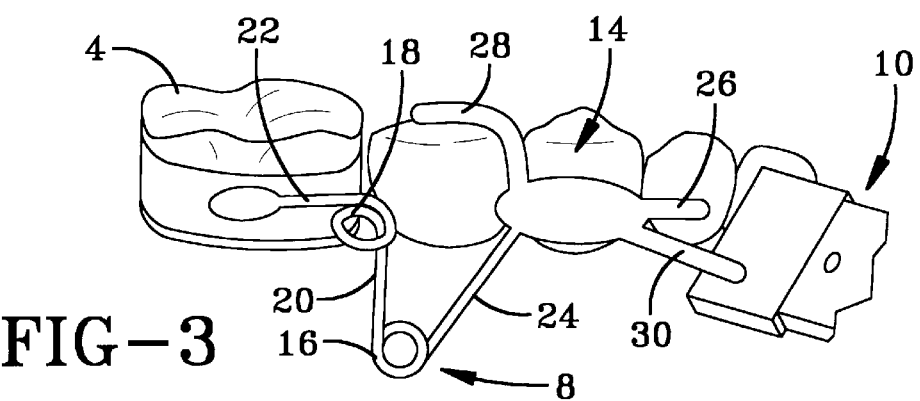
FIG. 3 is a cross-sectional view taken generally along the line 3—3 of FIG. 1.

As can be seen in FIGS. 2 and 3, helical spring apparatuses 6 and 8 are formed by a vertical helical spring 16 connected to a horizontal helical spring 18 by a helix connecting wire 20. An orthodontic band connecting wire 22 extends from horizontal helical spring 18 and is soldered to orthodontic band 2 as can be seen in FIG. 2, or orthodontic band 4 as can be seen in FIG. 3. A metal framework connecting wire 24 extends from vertical helical spring 16 to one of the metal framework assemblies 12 or 14, where it is soldered. During assembly of arch mandibular expander 1 metal framework connecting wire 24 is placed adjacent or on top of central rod member 26. Arm rod member 28 is placed adjacent to the central rod member 26, such that one end of arm rod member 28 touches central rod member 26, while the other end of arm rod member 28 extends away from the central rod member 26, and then curves into a parallel relationship with central rod member 26. Arm rod member 30 is positioned at a diagonal location with respect to arm rod member 28, and extends from the opposite side of central rod member 28 into a similar curved and parallel arrangement as arm rod member 28 and central rod member 26. A ball of solder is placed in the center of the central rod member 26 causing central rod member 26, arm rod member 28, arm rod member 30 and metal framework wire 24 to be in a permanently fixed relationship. Arm rod member 30 is then soldered to expansion screw mechanism 10 at one side of expansion screw mechanism 10. The assembly of the opposite metal framework is the same except that arm rod member 30 is soldered to the opposite side of expansion screw mechanism 10.

The use of the above arrangement to form metal framework assembly 12 and 14 provides an easy to assemble, inexpensive and durable mechanism for providing a stationary device for effecting expansion of the mandibular by expansion screw mechanism 10 and spring apparatuses 6 and 8. Further, the device can be positioned to be barely noticeable to an ordinary observer looking at a patient having expander 1 installed. It should be appreciated that metal framework assemblies 12 and 14 could be replaced by other devices or arrangements. The only requirement is that the device must be affixed to the teeth of a patient at a location between the lower molar and lower incisor teeth, and be attachable both to any expansion device provided near the incisor teeth, and to the spring apparatus for expanding and lengthening the teeth at the rear of the jaw.

Each expander is customized to the individual patient's mouth. Typically, the dimensions are obtained by impressions using conventional means, such as paste impressions or the like. Once the device is assembled, it can be placed into a patient's mouth. The orthodontic band 2 and 4 are placed over molars 3 and 5 and cemented into place. Expansion screw mechanism 10 is placed adjacent the inside of incisor teeth 40, 42, 44 and 46. Arm rod members 28 of metal framework 12 and 14 come to rest on premolars 50 and 52, respectively. The metal framework is then bonded to the premolars at arm rod member 28, preferably using white composite cement 49. Alternatively, metal framework 12 and 14 can be bonded at the opposite end of central rod member 26 to canine teeth 54 and 56, respectively. In some situations, it may be preferable to bond metal framework 12 and 14 at both positions.

The expander 1 can be activated inside or outside of the patient's mouth. The expander is activated by activating the vertical and horizontal loops of the spring apparatus. The vertical helical spring and horizontal helical spring can be activated by opening or stretching the loop and then by closing or returning the helical loop to its original position. Once activated, the vertical loop applies a posterior or rearward force on the molar band and thus causes the molar to push away from the incisor teeth. The horizontal helical spring 18 can also be activated by opening and reclosing the horizontal loop. This causes a rotational force on the molars. Helical connecting wire 20 can be bent, re-straightened and repositioned to provide a lateral or outward force on the molar. Once installed and activated, expander 1 can be adjusted periodically by the opening of expansion screw mechanism 10 using key opening 11, and readjusting the horizontal and vertical helical springs and corresponding connecting wire.

Figure 4:
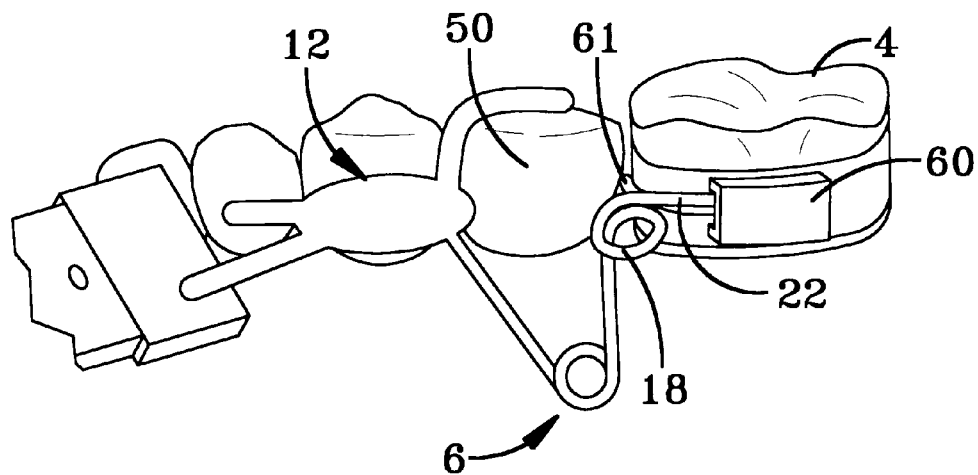
FIG. 4 is a partial side view of the mandibular arch expander of the present invention including an orthodontic band with a sheath.

Although expander 1 is installed as a single unit fixed device, it should be appreciated that it could be formed into removable parts. As can be seen in FIG. 4, orthodontic band connecting wire 22 includes an end section 61. End section 61 is bent into a parallel relationship with connecting wire 22. The bend is placed through a sheath or telescoping tube 60, as opposed to being directly cemented to molar band 4. The open end of end portion 61 is placed between molar tooth 4 and tooth 50. In this particular aspect of the invention, the molar bands can be cemented to the molars and then the metal framework can be bonded to the teeth. Band connecting wire 22 is formed from a double thickness arm and can be inserted into the sheath to apply the proper pressure after it has been adjusted. The purpose of the removable connecting wire 22 is to allow the device to be more easily adjusted and placed into position. Further, it allows for easier additional adjustments of vertical helical spring 16, horizontal helical spring 18 and connecting wire 20.

Figure 5:
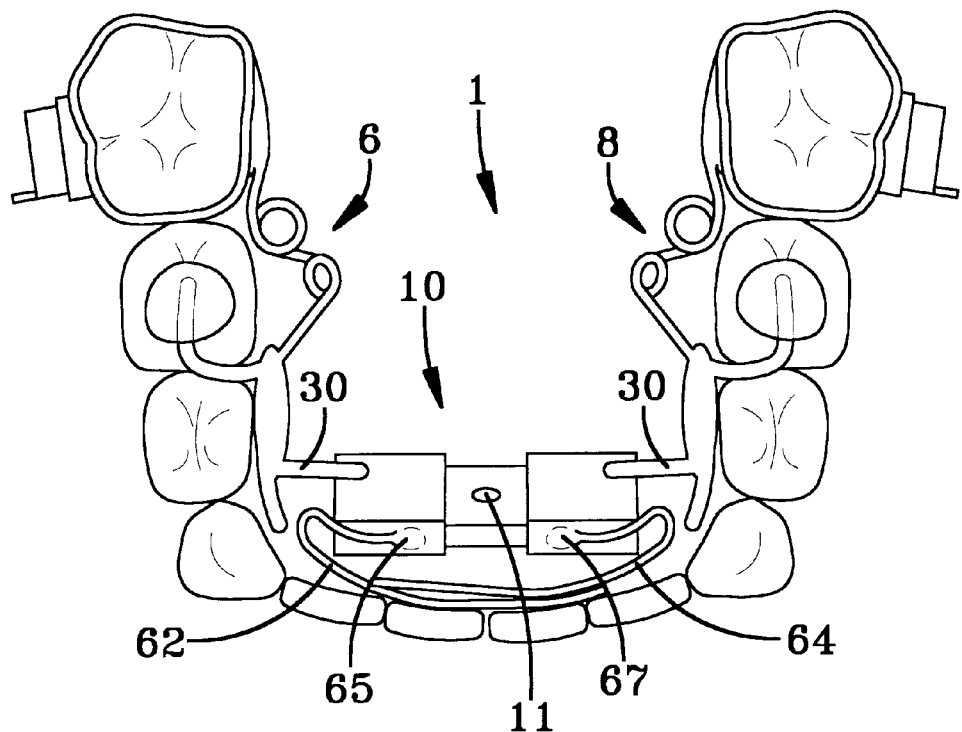
FIG. 5 is a plan view of the mandibular arch expander of the present invention attached to a mold of the mandibular arch including arm members extending toward the front incisor teeth.

In some situations, it is desired to get the front incisor teeth positioned slightly better in the widened jaw prior to placing braces on the teeth. As can be seen in FIG. 5, two criss-crossing arm members 62 and 64 are positioned in a gap between expansion screw mechanism 10 and the front incisor teeth. Arm members 62 and 64 can be soldered to expansion screw mechanism 10 at points 65 and 67, respectively, which are located at the front of expansion screw mechanism 10. Arm members 62 and 64 may be soldered to arm member 30 at opposite ends of expansion screw mechanism 10. Preferably, the arms are made of stainless steel. The arms can be activated by bending them outward away from the device and returning them to their original position. Once the expander is seated and arm members 62 and 64 activated, the arm members apply pressure outwards to push the teeth into the space created by the developer 1. In some situations it may be desired to only use on arm member applying pressure between the two center incisor teeth or the two left or right incisor teeth depending on the patient's particular needs.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar they come within the scope of the invention as claimed or the equivalence thereof.

What is claimed is:

1. A lower mandibular arch expander for moving the lower teeth of an individual in a better alignment with the upper teeth, said expander comprising:

a first orthodontic band and a second orthodontic band, each of said bands being adapted to fit over a lower molar tooth;

first and second attachment means, each of said attachment means being adapted to fit over a lower molar tooth;

a first spring means located between said first attachment means and said first orthodontic band, said first spring means being actuable for applying both rotational and linear forces simultaneously on a first molar tooth when said first orthodontic band surrounds and is affixed to the first molar tooth, wherein said first spring means comprises a first vertical helical spring actuable to apply force to the first molar tooth both back and away from the lower incisor teeth, a first horizontal helical spring actuable to apply a rotational force to the first molar tooth and a first connecting wire connecting said first horizontal helical spring and said first vertical helical spring and being actuable to apply force toward the cheek of an individual, when said first orthodontic band surrounds and is affixed to the first molar tooth; and a second spring means located between said second attachment means and said second orthodontic band, said second spring means being actuable for applying both rotational and linear forces simultaneously on a second molar tooth when said second orthodontic band surrounds and is affixed to the second molar tooth, wherein said second spring means is comprised of a second vertical helical spring actuable to apply force to the second molar tooth both back and away from the lower incisor teeth, a second horizontal helical spring actuable to apply a rotational force to the second molar tooth and a second connecting wire connecting said second horizontal helical spring and said second vertical helical spring and being actuable to apply force toward the cheek of an individual, when said second orthodontic band surrounds and is affixed to the second molar tooth.

2. A lower mandibular arch expander as defined in claim 1, wherein the linear forces applied by said first and second spring means on each molar tooth include a linear force both back and away from the lower incisor teeth and a linear force on each molar tooth out toward an individual's cheek.

3. A lower mandibular arch expander as defined in claim 1, wherein each of said attachment means is comprised of a metal framework assembly having at least one rod member being adaptable to be bonded to at least one tooth at a location between the molar tooth and the front canine teeth.

4. A lower mandibular arch expander as defined in claim 1, and further including a first sheath attached to said first orthodontic band and a second sheath attached to said second orthodontic band, said first spring means including a first band connecting rod being releasably engagable in said first sheath and said second spring means including a second band connecting rod being releasably engagable in said second sheath.

5. A lower mandibular arch expander as defined in claim 1, and further including expansion means for widening the mandibular arch at a location near the front incisor teeth of an individual, said expansion means being disposed between said first and second attachment means.

6. A lower mandibular arch expander as defined in claim 5, wherein said expansion means is an expansion screw.

7. A lower mandibular arch expander as defined in claim 5, wherein each of said attachment means further includes at least one rid member for affixing to said expansion means.

8. A lower mandibular arch expander as defined in claim 5, and further including at least one arm member extending from said expansion means adapted to apply force to the front canine teeth of an individual.

9. A lower mandibular arch expander for moving the lower teeth of an individual in better alignment with the upper teeth, said expander comprising:

a first orthodontic band and a second orthodontic band, each of said bands being adapted to fit over a lower molar tooth;

first and second attachment means, each of said attachment means being adapted to be affixed to at least one tooth;

a first spring means located between said first attachment means and said first orthodontic band, said first spring means being actuable for applying both rotational and linear forces on a first molar tooth when said first orthodontic band surrounds and is affixed to the first molar tooth;

a second spring means located between said second attachment means and second orthodontic band, said second spring means being actuable for applying both rotational and linear forces on a second molar tooth when said second orthodontic band surrounds and is affixed to the second molar tooth; and expansion means disposed between said first and second attachment means for widening the mandibular arch at a location between said first and second attachment means.

10. A lower mandibular arch expander as defined in claim 9, wherein said first spring means is comprised of a first vertical helical spring actuable to apply force to the first molar tooth both back and away from the lower incisor teeth, and a first horizontal helical spring actuable to apply a rotational force to the first molar tooth and a first connecting wire actuable to apply force toward the cheek of an individual, when said first orthodontic band surrounds and is affixed to the first molar tooth, said first connecting wire connecting said first horizontal helical spring and said first vertical helical spring; and said second spring means is comprised of a second vertical helical spring actuable to apply force to the second molar tooth both back and away from the lower incisor teeth, and a second horizontal helical spring actuable to apply a rotational force to the second molar tooth and a second connecting wire actuable to apply force toward the cheek of an individual, when said second orthodontic band surrounds and is affixed to the second molar tooth, said second connecting wire connecting said second horizontal helical spring and said second vertical helical spring.

11. A lower mandibular arch expander as defined in claim 9, wherein said expansion means is an expansion screw.

12. A lower mandibular arch expander as defined in claim 9, wherein each of said attachment means further includes at least one rod member for affixing to said expansion means.

13. A lower mandibular arch expander as defined in claim 9, and further including at least one arm member extending from said expansion means adapted to apply force to the front canine teeth of an individual.

14. A lower mandibular arch expander as defined in claim 9, wherein the linear forces applied by said first and second spring means on each molar tooth include a linear force both back and away from the lower incisor teeth and a linear force on each molar tooth out toward an individual's cheek.

15. A lower mandibular arch expander as defined in claim 9, wherein each of said attachment means is comprised of a metal framework assembly having at least one rod member being adaptable to be bonded to at least one tooth at a location between the molar tooth and the front canine teeth.

16. A lower mandibular arch expander as defined in claim 9, and further including a first sheath attached to said first orthodontic band and a second sheath attached to said second orthodontic band, said first spring means including a first band connecting rod being releasably engagable in said first sheath and said second spring means including a second band connecting rod being releasably engagable in said second sheath.

17. A lower mandibular arch expander for moving the lower teeth of an individual in better alignment with the upper teeth of the individual, said expander comprising:

an orthodontic band adapted to fit over a lower molar tooth;

attachment means adapted to be bonded to at least one tooth;

spring means located between said attachment means and said orthodontic band, said spring means being actuable for applying both rotational and linear forces simultaneously on a molar tooth when said orthodontic band surrounds and is affixed to the molar tooth, wherein said spring means is comprised of a vertical helical spring actuable to apply force to the molar tooth both back and away from the lower incisor teeth, a horizontal helical spring actuable to apply a rotational force to the molar tooth and a connecting wire connecting said horizontal helical spring and said vertical helical spring and being actuable to apply force toward the cheek of an individual when said orthodontic band surrounds and is affixed to the molar tooth.

18. A lower mandibular arch expander as defined in claim 17, wherein the linear forces applied by said spring means on the molar tooth include a linear force both back and away from the lower incisor teeth of an individual and a linear force out toward the individual's cheek.

19. A lower mandibular arch expander as defined in claim 17, wherein said attachment means is comprised of a metal framework assembly having at least one rod member being adaptable to be bonded to at least one tooth.

20. A lower mandibular arch expander as defined in claim 17, and further including a sheath attached to said orthodontic band, and said springs means further including a band connecting rod releasably engagable in said sheath.

21. A lower mandibular arch expander for moving the lower teeth of an individual in better alignment with the upper teeth, said expander comprising:

a first orthodontic band and a second orthodontic band, each of said bands being adapted to fit over a lower molar tooth;

a first and second metal framework assembly, each of said metal framework assemblies including at least one rod member adaptable to being bonded to at least one tooth between the molar tooth and the incisor teeth;

a first spring means disposed between said first metal framework assembly and said first orthodontic band, said first spring means comprising a first vertical helical spring actuable to apply force to the first molar tooth both back and away from the lower incisor teeth, a first horizontal helical spring actuable to apply a rotational force to the first molar tooth and a first connecting wire actuable to apply force toward the cheek of an individual, when said first orthodontic band surrounds and is affixed to the first molar tooth, said first connecting wire connecting said first horizontal helical spring and said first vertical helical spring; and a second spring means disposed between said second metal framework assembly and said second orthodontic band, said second spring means comprising a second vertical helical spring actuable to apply force to the second molar tooth both back and away from the lower incisor teeth, a second horizontal helical spring actuable to apply a rotational force to the second molar tooth and a second connecting wire actuable to apply force toward the cheek of an individual, when said second orthodontic band surrounds and is affixed to the second molar tooth, said second connecting wire connecting said second horizontal helical spring and said second vertical helical spring.

22. A lower mandibular arch expander as defined in claim 21, wherein each of said metal framework assemblies further includes at least one rod member for affixing to said expansion means.

23. A lower mandibular arch expander as defined in claim 21, and further including at least one arm member extending from said expansion means adapted to apply force to the front incisor teeth of an individual.

24. A lower mandibular arch expander as defined in claim 21, and further including a first sheath attached to said first orthodontic band and a second sheath attached to said second orthodontic band, said first springs means including a first band connecting rod releasably engagable in said first sheath and said second spring means including a second band connecting rod releasably engagable in said second sheath.

25. A lower mandibular arch expander as defined in claim 21, and further including expansion means for widening the mandibular arch at a location near the front incisor teeth of an individual, said expansion means being disposed between said first and second metal framework assemblies.

26. A lower mandibular arch expander as defined in claim 25, wherein said expansion means is an expansion screw.

* * * * *